US012773105B2

(12) United States Patent
Intintoli et al.

(10) Patent No.: US 12,773,105 B2
(45) Date of Patent: Oct. 27, 2026

(54) FULLY INTEGRATED, DISPOSABLE TISSUE VISUALIZATION DEVICE WITH OFF AXIS VIEWING

(71) Applicant: Trice Medical, Inc., Malvern, PA (US)

(72) Inventors: Alfred J. Intintoli, Malvern, PA (US); Frederick H. Hardenbrook, Malvern, PA (US); Stefanie A. Hurowitz, Malvern, PA (US)

(73) Assignee: Trice Medical, Inc., Malvern, PA (US)

( * ) Notice: Subject to any disclaimer, the term of this patent is extended or adjusted under 35 U.S.C. 154(b) by 438 days.

(21) Appl. No.: 17/759,777

(22) PCT Filed: Jan. 25, 2021

(86) PCT No.: PCT/US2021/014949
§ 371 (c)(1),
(2) Date: Jul. 29, 2022

(87) PCT Pub. No.: WO2021/154657
PCT Pub. Date: Aug. 5, 2021

(65) Prior Publication Data

US 2023/0065294 A1 Mar. 2, 2023

Related U.S. Application Data

(60) Provisional application No. 62/967,447, filed on Jan. 29, 2020.

(51) Int. Cl.
*A61B 1/07* (2006.01)
*A61B 1/00* (2006.01)

(52) U.S. Cl.
CPC ............ *A61B 1/07* (2013.01); *A61B 1/00163* (2013.01)

(58) Field of Classification Search
CPC ............ A61B 1/00096; A61B 1/00174; A61B 1/00177; A61B 1/00179; A61B 1/00183;
(Continued)

(56) References Cited

U.S. PATENT DOCUMENTS

| | | | | |
|---|---|---|---|---|
| 3,941,121 A | | 3/1976 | Olinger et al. | |
| 4,138,192 A | * | 2/1979 | Yamasita ........... | G02B 23/2423 359/834 |

(Continued)

FOREIGN PATENT DOCUMENTS

| | | | | |
|---|---|---|---|---|
| CN | 106343943 B | 12/2017 | | |
| WO | WO-2017150154 A1 * | 9/2017 | .............. | A61B 1/07 |
| WO | WO 2021/154657 A9 | 8/2021 | | |

OTHER PUBLICATIONS

International Search Report issued for International Patent Application No. PCT/US21/14949, dated Apr. 28, 2021 in 1 page.

(Continued)

*Primary Examiner* — Michael J Carey
*Assistant Examiner* — Stephen Floyd London
(74) *Attorney, Agent, or Firm* — Knobbe, Martens, Olson & Bear LLP

(57) ABSTRACT

The present invention relates to a fully integrated sterilizable one time use disposable tissue visualization device and methods for using such devices. Preferred embodiments of the invention facilitate the visualization of an internal tissue site while ausing a minimum of damage to the surrounding tissue. Further preferred embodiments may allow for the delivery of fluids and other treatment to an internal tissue site.

18 Claims, 16 Drawing Sheets

(58) Field of Classification Search

CPC ........... A61B 1/05; A61B 1/051; A61B 1/053; A61B 1/00098; A61B 1/00137; G02B 7/1805

See application file for complete search history.

(56) References Cited

U.S. PATENT DOCUMENTS

| | | | | |
|---|---|---|---|---|
| 4,727,859 | A * | 3/1988 | Lia | G02B 23/2423 600/170 |
| 4,815,833 | A * | 3/1989 | Zobel | G02B 23/243 359/833 |
| 5,416,638 | A * | 5/1995 | Broome | A61B 1/055 348/E7.087 |
| 5,460,182 | A | 10/1995 | Goodman et al. | |
| 5,554,100 | A | 9/1996 | Leiner et al. | |
| 5,643,176 | A * | 7/1997 | Persidsky | A61B 1/00183 359/833 |
| 6,537,209 | B1 * | 3/2003 | Pinkhasik | A61B 1/00101 600/176 |
| 7,713,189 | B2 | 5/2010 | Hanke | |
| 7,927,272 | B2 | 4/2011 | Bayer et al. | |
| 8,439,830 | B2 | 5/2013 | Mckinley et al. | |
| 8,460,182 | B2 | 6/2013 | Ouyang et al. | |
| 9,247,862 | B2 | 2/2016 | Shen et al. | |
| 9,370,295 | B2 | 6/2016 | Kienzel et al. | |
| 10,092,176 | B2 | 10/2018 | Kienzel et al. | |
| 10,092,315 | B2 | 10/2018 | Jansen et al. | |
| 2008/0208006 | A1 * | 8/2008 | Farr | A61B 1/0676 600/178 |
| 2009/0264706 | A1 * | 10/2009 | Bala | A61B 1/00101 600/160 |
| 2011/0009694 | A1 | 1/2011 | Schultz et al. | |
| 2014/0135577 | A1 * | 5/2014 | Baumann | A61B 1/00179 600/109 |
| 2016/0345804 | A1 | 12/2016 | Wieters et al. | |
| 2017/0042408 | A1 | 2/2017 | Washburn et al. | |
| 2017/0112369 | A1 * | 4/2017 | Czupalla | A61B 1/00193 |
| 2017/0325664 | A1 | 11/2017 | Kirma et al. | |
| 2020/0037861 | A1 * | 2/2020 | Yamaya | A61B 1/00135 |
| 2020/0178772 | A1 * | 6/2020 | Sekiguchi | A61B 1/307 |
| 2020/0225446 | A1 * | 7/2020 | Wieters | A61B 1/00096 |
| 2020/0237195 | A1 * | 7/2020 | Wieters | G02B 23/2476 |

OTHER PUBLICATIONS

Bader et al., “The “all-seeing needle”: initial results of an optical puncture system confirming access in percutaneous nephrolithotomy”; Eur Urol. Jun. 2011;59(6):1054-9. Epub, Apr. 1, 2011. https://www.ncbi.nlm.nih.gov/pubmed/21477921.

Han et al., “Handheld forward-imaging needle endoscope for ophthalmic optical coherence tomography inspection”; J. Biomed. Opt. Mar-Apr. 2008;13(2):020505. https://www.ncbi.nlm.nih.gov/pubmed/18465947.

International Search Report and Written Opinion for Application No. PCT/US2021/014949, mailed Apr. 28, 2021, 12 pages.

* cited by examiner

FULLY INTEGRATED, DISPOSABLE TISSUE VISUALIZATION DEVICE WITH OFF AXIS VIEWING

CROSS-REFERENCE TO RELATED APPLICATIONS

This application claims priority to U.S. Provisional Application No. 62/967447, entitled FULLY INTEGRATED, DISPOSABLE TISSUE VISUALIZATION DEVICE WITH OFF AXIS VIEWING, filed on Jan. 29, 2020. The entirety of this application is hereby incorporated by reference in its entirety.

BACKGROUND

Field of the Invention

This application describes embodiments of apparatuses, methods, and systems for the visualization of tissues with off axis viewing.

Description of the Related Art

Traditional surgical procedures, both therapeutic and diagnostic, for pathologies located within the body can cause significant trauma to the intervening tissues. These procedures often require a long incision, extensive muscle stripping, prolonged retraction of tissues, denervation and devascularization of tissue. Such procedures can require operating room time of several hours followed by several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

Treatment of internal tissue sites, such as the treatment of an orthopedic joint, often requires visualization of the target internal tissues. However, proper visualization of an internal tissue site can be expensive and time-consuming to schedule, such as when magnetic resonance imaging (MRI) is required. Further, other modes of imaging can potentially damage the tissue site, leading to poor diagnosis and extended recovery time. Consequently, there is need for improved devices and methods for visualization of an internal tissue site.

SUMMARY

Embodiments of the present invention relate to tissue visualization devices, methods, and systems. In some examples, an integrated disposable tissue visualization device with off axis viewing, includes an elongate rigid tubular probe, extending along a longitudinal axis between a proximal end and a distal end, a camera, an illumination element, and a prism. In some examples, the prism provides off-axis viewing of a target tissue at an angle range of at least 25°. In some examples, the angle range includes an angle range of least 45°, at least 60°, at least 75° or at least 90°. The prism may have high index of refraction material of at least 2.0.

The device may include a sled configured to receive the camera and the prism. The camera may be positioned within an enclosed area of the sled. The prism may be positioned at a distal end of the sled. The sled may include an angled surface configured to receive the prism. The prism can include an angled surface configured to be positioned on the angled surface of the sled. The slope of the angled surface of the prism can be substantially similar a slope of the angled surface of the sled.

In some examples, the sled, the camera, and a potted housing may form a cylindrical assembly. In some examples, the sled and a potted housing form a cylindrical assembly with the camera positioned therein. In some examples, the distal surface of the cylindrical assembly can include an angled surface. The cylindrical assembly can further include the prism, wherein the prism is positioned on the angled distal surface of the cylindrical assembly. The prism can include a flat surface configured to form a flat distal end of the cylindrical assembly. The cylindrical assembly can be positioned at the distal end of the elongate rigid tubular probe. The illumination element can be positioned circumferentially around the cylindrical assembly. The device can further include a covering that surrounds the cylindrical assembly. The illumination element may include an illumination fiber or light emitting diodes. The prism can be configured to refract an image of the target tissue to be received by the camera. The target tissue can be an orthopedic joint.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

Figure 1:
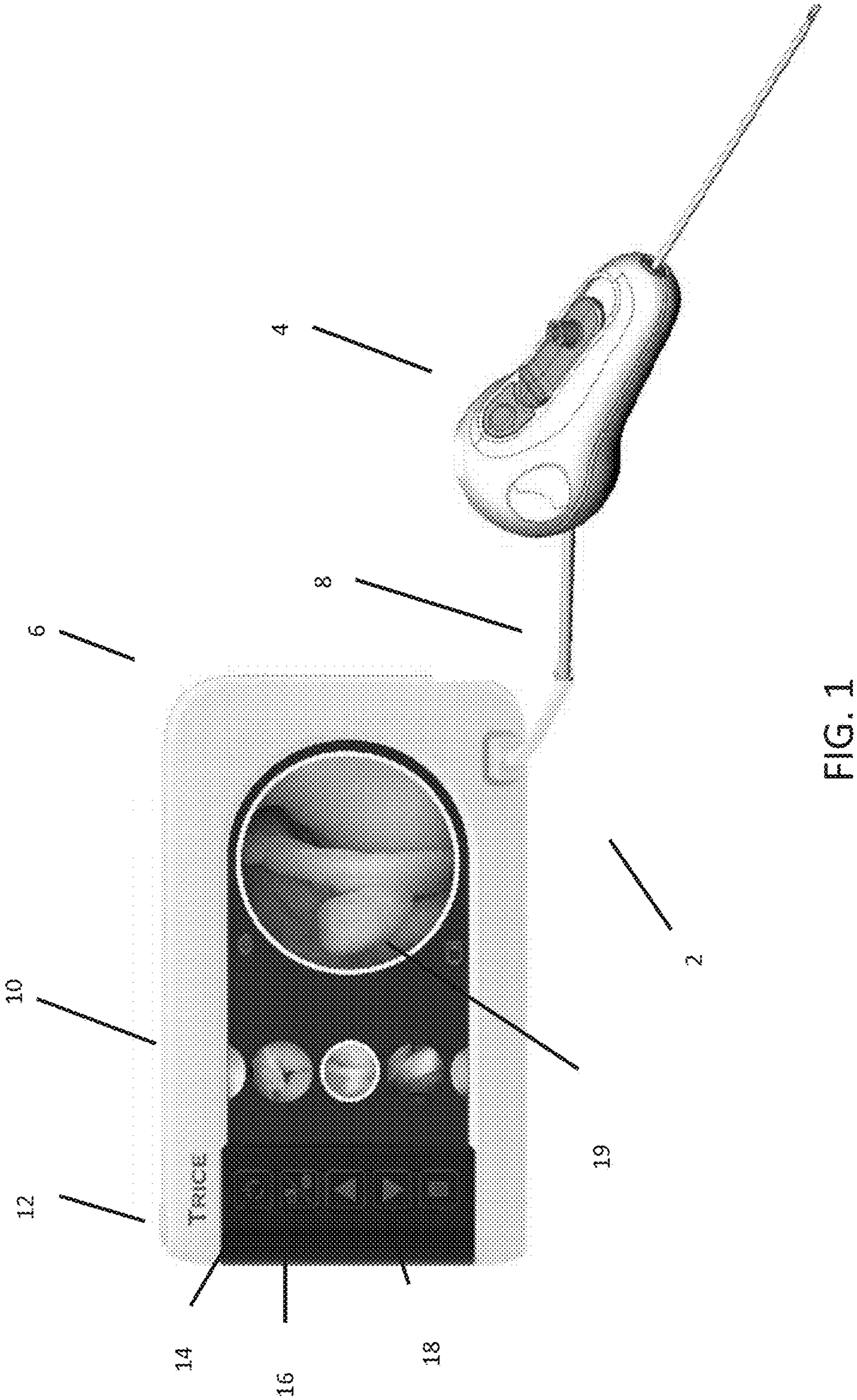
FIG. 1 illustrates an embodiment of a tissue visualization system.

Examples disclosed in this section or elsewhere in this application relate to minimally invasive tissue visualization and access systems and devices. Also provided are methods of using the systems in imaging applications, as well as kits for performing the methods. Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. Where a range of values is provided, it is understood that each intervening value between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the terms "about," "around," and "approximately." These terms are used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the invention include minimally invasive imaging and visualization systems. In some examples, imaging systems of the invention are minimally invasive, such that they may be introduced to an internal target site of a patient, for example, a spinal location that is near or inside of an intervertebral disc or an orthopedic joint capsule, through a minimal incision.

FIG. 1 illustrates an embodiment of a system 2 for the visualization of an interior tissue site. In some examples, a tissue visualization system 2 includes: a tissue visualization device 4, a controller 6, and a cable 8 that provides electrical communication between the controller 6 and the tissue visualization device 4.

The tissue visualization device 4 may include an elongated body having a proximal and distal end, where the elongated body is dimensioned to be slidably moved through the internal passageway of an access device or directly through tissue without the use of an additional access device. When designed for use in knee joint procedures, the elongated body is dimensioned to access the capsule of the knee joint. The elongated body may be solid or include one or more lumens, such that it may be viewed as a catheter. The term "catheter" is employed in its conventional sense to refer to a hollow, flexible or semi-rigid tube configured to be inserted into a body. Catheters of the invention may include a single lumen, or two or more lumens, e.g., three or more lumens, etc, as desired. Depending on the particular embodiment, the elongated bodies may be flexible or rigid, and may be fabricated from any convenient material.

The tissue visualization system 2 can also include visualization sensors and illumination elements. In certain examples, these visualization sensors are positioned within a handle at the proximal end of the device. The system may include one or more visualization sensors at the proximal end of the device and one or more illumination elements that are located among the distal and/or proximal ends of the elongated body. In particular examples, one or more visualization sensors may be located in the distal end of the device such as within the distal end of the elongated body.

Similarly, with respect to the illumination elements, examples of the systems include those systems where one or more illumination elements are located at the distal and/or proximal end of the elongated body. Examples of the systems also include those systems where one illumination element is located at the distal and/or proximal end of the elongated body and another illumination element is located at the distal and/or proximal end of the access device. Furthermore, examples of the systems include those systems where one or more illumination elements are located at the proximal end of the device and light is propagated via wave guides such as a fiber optic bundle towards the distal end of the device.

In certain examples, the systems of the invention are used in conjunction with the controller 6 configured to control illumination of the illumination elements and/or capture of images (e.g., as still images or video output) from the visualization sensors. This controller may take a variety of different formats, including hardware, software and combinations thereof. The controller 6 may be physically located relative to the elongated body at any convenient location such as at the proximal end of the system. In certain examples, the controller 6 may be distinct from the system components, i.e., elongated body, such that a controller interface is provided that is distinct from the proximal handle, or the controller may be integral with the proximal handle.

In certain examples, the controller 6 may comprise a housing having a data port such as an USB 10 and a camera button 12. The camera button 12 may activate the system to collect and store a still or moving image. The controller 6 may further comprise a power button 14, a mode switch button 16, and brightness controls 18. The controller 6 can further comprise a display such as a screen 19 for displaying still images and/or video. The system may take video or still images collected and displayed in real-time or saved for later for analysis at a later time. In some embodiments, it may be desirable to remove cable 8 and provide instead a wireless communication link between the probe and the monitor and possibly also to a centralized medical records storage and/or evaluation location. In certain examples, the tissue visualization systems as described in U.S. applications Ser. Nos. 14/308,167 and 15/234,999 (the disclosures of which are herein incorporated by reference) is present in the system described herein.

The distal end of the elongated body of the tissue visualization device 4 may be configured for front viewing and/or side-viewing, as desired. The elongated body may be configured to provide image data from both the front and the side, e.g., where the primary viewing axis from the distal end of the elongated body extends at an angle that is greater than about 2° or 5° or 10° or 15° relative to the longitudinal axis of the elongated body.

The tissue visualization device 4 may have an increased degree of off-axis viewing at the distal end of the elongate body. In some examples, the off-axis viewing may be at least 25° relative to the longitudinal axis of the elongated body. In some examples, the off-axis viewing may be about 25°, 30°, 35°, 40°, or 45° or more relative to the longitudinal axis of the elongated body.

The increased degree off-axis viewing may be achieved with the use of a refractive prism. In certain examples, a desired direction of view may be reached by positioning a prism at the distal end of the elongated body. Such a prism may provide a direction of view, for example: providing a direction of view 30° from the axis of the elongated body. In some embodiments, the angle may be much smaller, such as between 0°-15°. In further embodiments the angle may range from 15°-45°. In some embodiments, the angle may be at least 45°, at least 60°, at least 75° or at least 90° or more.

Figure 2:
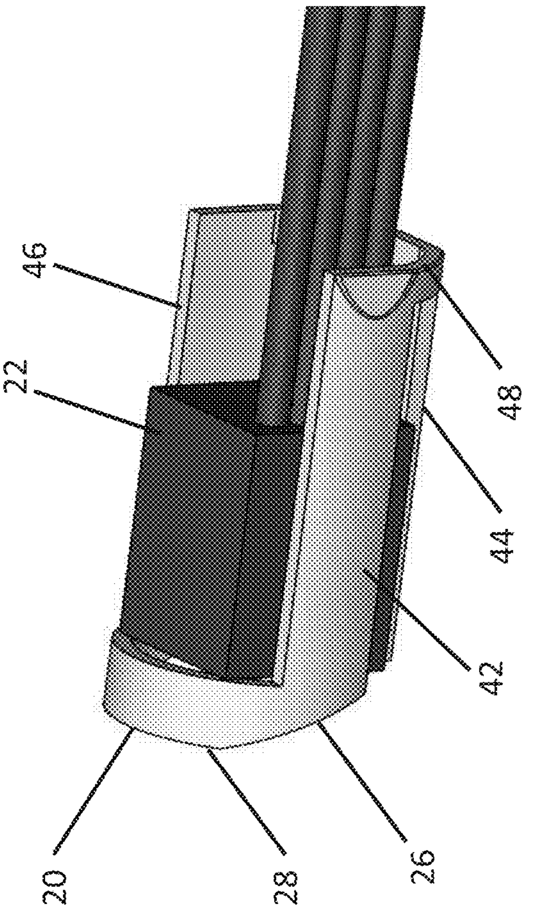
FIGS. 2 illustrates a camera and sled of the tissue visualization device.

FIG. 2 illustrates a visualization sensor or camera 22 and a sled 20 of the tissue visualization device 4. The sled 20 can be a housing, a frame, or cradle that is configured to receive the camera 22 (as shown in FIG. 2) and the refractive prism 30 (as described below). The refractive prism 30 can provide off axis viewing at various angles, such as 30 degrees. In further examples, the off axis angle may range from 15°-45°. In some embodiments, the off-axis angle may be at least 45°, at least 60°, at least 75° or at least 90° or more. As shown in FIG. 2, the camera 22 can be received within an internal or enclosed area defined by the sled 20. The camera 22 can be attached to the sled 20 in several different ways, such as by snap fit, fraction fit, mechanical fastening, or adhesive. The sled 20 may have an angled distal surface 26.

The sled 20 can include at least three side portions 42, 44, 46. The side portions 42, 44, 46 may be positioned such that their lengths are parallel to one another. The side portions 42, 44, 46 be considered a partial shell or partial cylindrical surface with slots between the side portions 42, 44, 46. The sled 20 can optionally include a distal portion 28 that connects one or more of the three side portions 42, 44, 46 on the respective distal ends of each of the side portions 42, 44, 46. In some examples, the distal portion 28 can connect the first and second side portions 42, 44. In some examples, the distal portion can be connected to all three side portions 42, 44, 46. The distal portion 28 can have a partial or semi-circular cross section. The three side portions 42, 44, 46 and optionally the distal portion 28 can form a recess that receives the camera 22. The distal portion 28 can include an angled distal surface 26. In some embodiments, the angle distal surface 26 may extend partially on the end of the distal portion 28, such that the remaining end surface of the distal portion may be flat. In some examples, the angled distal surface 26 may extend on the entire end surface of the distal portion 28, which can allow the prism and the sled to be positioned close together with a minimal gap. The sled 20 can also include a proximal portion 48 that connects one or more of the three side portions 42, 44, 46 on the respective proximal ends of each of the side portions 42, 44, 46. The proximal portion 48 can also have a partial or semi-circular cross section.

Figure 3B:
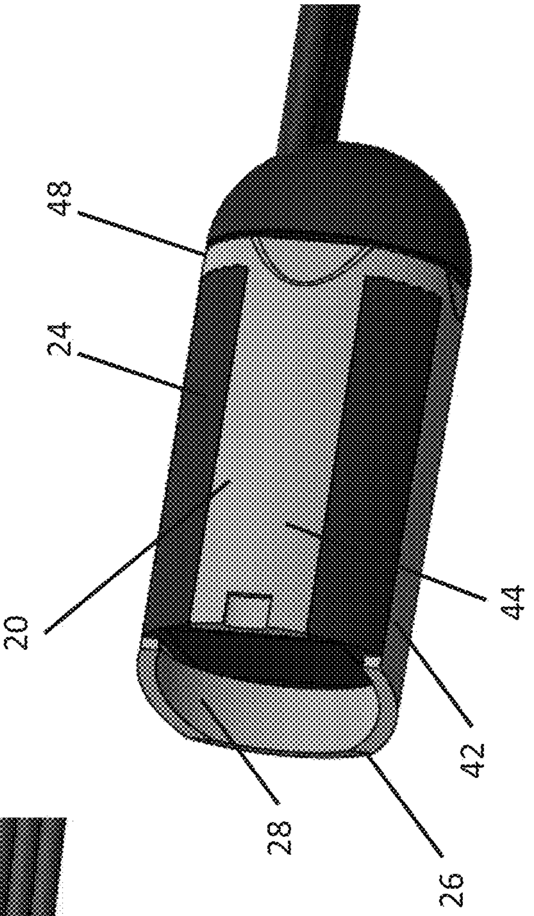
FIGS. 3A-B illustrate views of the camera and sled as illustrated in FIG. 2 with a surrounding potting compound.
Figure 3A:
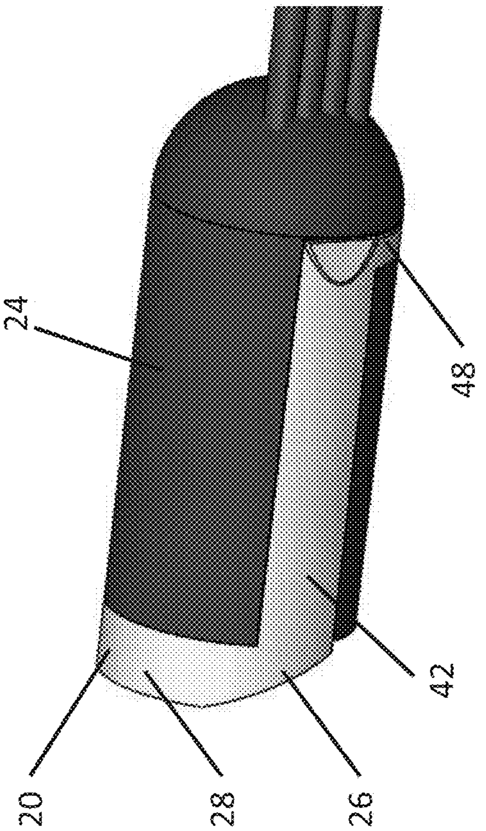

FIGS. 3A-3B illustrate views of the potting (adhesive) forming the potted housing 24 and sled 20 as illustrated in FIG. 2 with a surrounding potted housing 24 attached to the sled 20. The potted housing 24 can have a cylindrical surface. The potted housing 24 be received by or engage with the sled 20. The potted housing 24 can have a substantially cylindrical surface such that the side portions 42, 44, 46 of the sled 20 can be positioned around the cylindrical surface of the potted housing 24. The potted housing 24 can have a partial cylindrical surface that corresponds to the partial cylindrical surface of the sled 20. A potting compound can be used to encapsulate the sled 20. In some examples, the sled 20 is placed in an external mold. The potting compound can flow into spaces surrounding the sled 20 in the external mold to form the potted housing 24. In some examples, the side portions 42, 44, 46 of the sled 20 can be friction fit onto the potted housing 24. In some examples, the distal portion 28 and/or the proximal portion 48 can be partially cylindrical such that the inner surface is friction fit around the outer cylindrical surface of the potted housing 24. The sled 20 can attach the camera 22 positioned within the recess of the sled 20 to the potted housing 24. The potted housing 24 can be attached to the sled 20 and the camera 22 to together form a cylinder or a cylindrical assembly. The camera 22, the potted housing 24 and the sled 20 can together form a cylindrical assembly or cylinder. The potted housing 24 and the sled 20 can together form a cylindrical assembly or cylinder that holds the camera 22 therein. The angled distal surface 26 of the sled 20 can be positioned at the end of the cylindrical assembly, such that the cylindrical assembly can have an angled distal surface 26 at a distal end of the cylindrical assembly. The potted housing 24 can be secured to the sled 20, such as by snap fit, fraction fit, mechanical fastening, or adhesive.

Figure 4B:
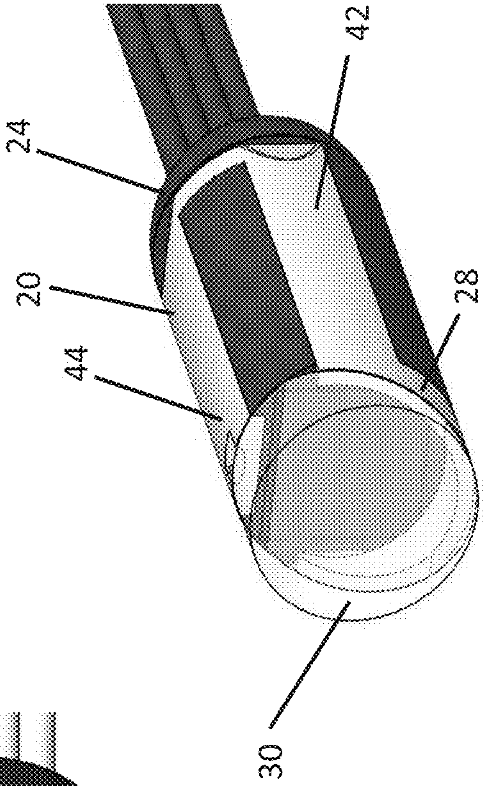
FIGS. 4A-B illustrate views of the camera and sled as illustrated in FIGS. 3A-3B with a prism.
Figure 4A:
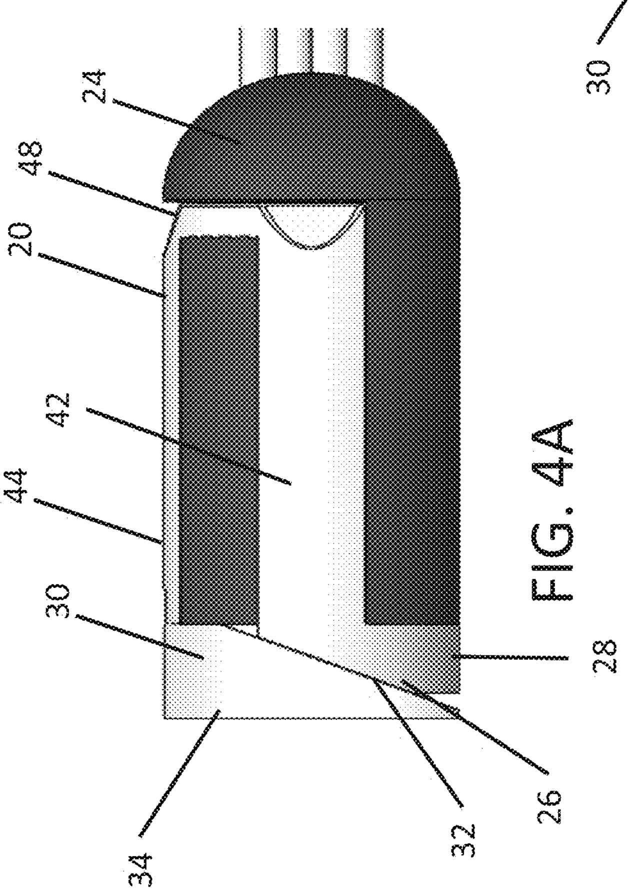

FIGS. 4A-B illustrate views of the potted housing 24 and sled 20 with a prism 30. The refractive prism 30 may be cubic zirconium or any other suitable material. The refractive prism 30 may have a refractive index of at least 2, such as between 2.10 to 2.30, between 2.14 to 2.20, or between 2.15 to 2.18. The high index of refraction advantageously allows the refractive prism 30 to be small in size. The sled 20 can receive a refractive prism 30 on the angled surface 26 of the sled 20. One side of the refractive prism 30 may have an angled or sloped surface 32. The angle of the distal surface 26 of the sled 20 can match or have substantially the same angle of the angled or sloped surface 32 of the refractive prism 30. An opposite side of the refractive prism 30 may have a flat surface 34. The flat surface 34 of the prism 30 can be positioned at the end of the sled 20 or the cylindrical assembly to form a flat distal end of the cylindrical assembly. The prism 30 may be attached to the sled 20 in various ways, such as by adhesive. The refractive prism 30 can provide off axis viewing, such as 25°. In further examples, the off axis angle may range from 15°-45°. In some embodiments, the off-axis angle may be at least 30°, at least 45°, at least 60°, at least 75° or at least 90° or more.

Figure 4E:
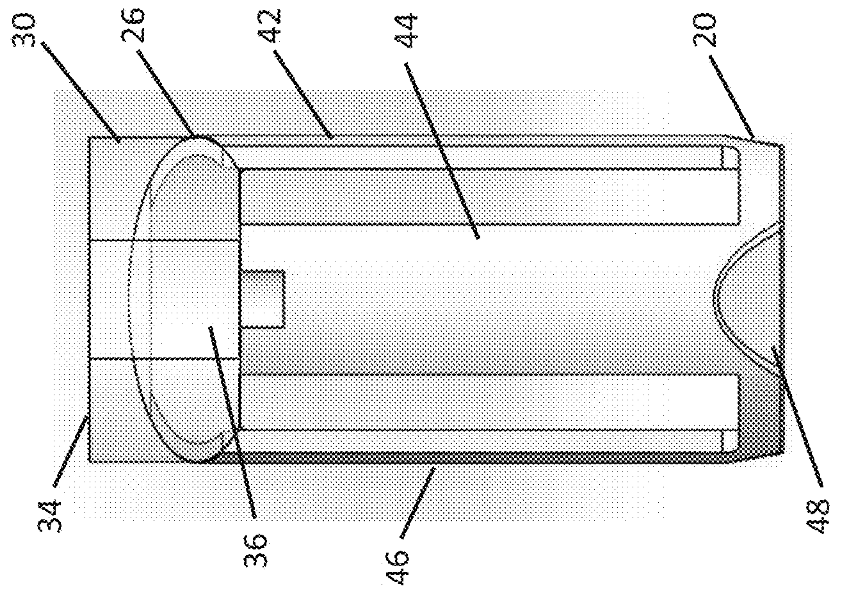
FIGS. 4C-4E illustrate views of the camera and sled as illustrated in FIGS. 4A-4B with another example of a prism.
Figure 4D:
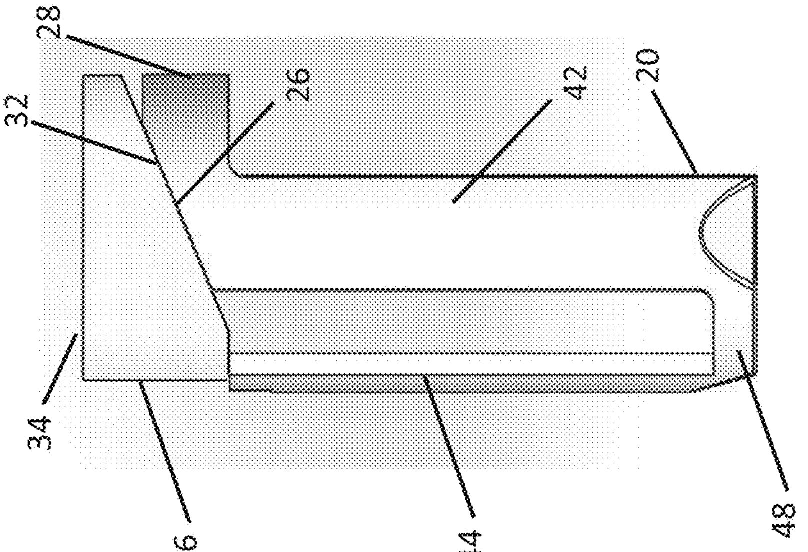
Figure 4C:
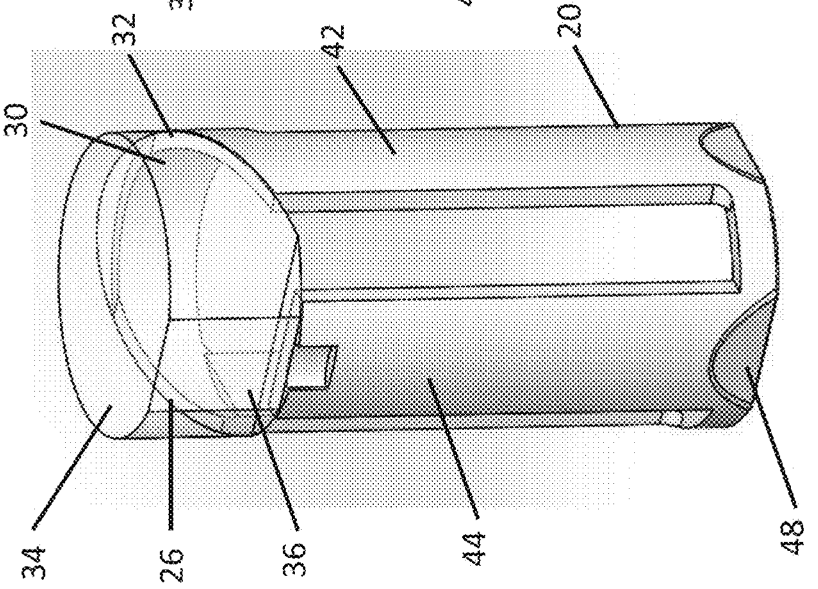

FIGS. 4C-4E illustrate views of the camera and sled as illustrated in FIGS. 4A-4B with another example of a prism. The refractive prism 30 can be similar to the prism 30 described in FIGS. 4A-4B but include a flat side or notch 36 on one side. The flat side 36 can allow alignment of the prism 30 with the sled 20. The flat side 36 or notch 36 can be aligned with a certain portion of the sled 20, such as the second side portion 44 of the sled. The flat side or notch 36 of the prism 30 may facilitate proper alignment of the angled surface 32 of the prism with the corresponding angled surface 26 of the sled 20.

Figure 5:
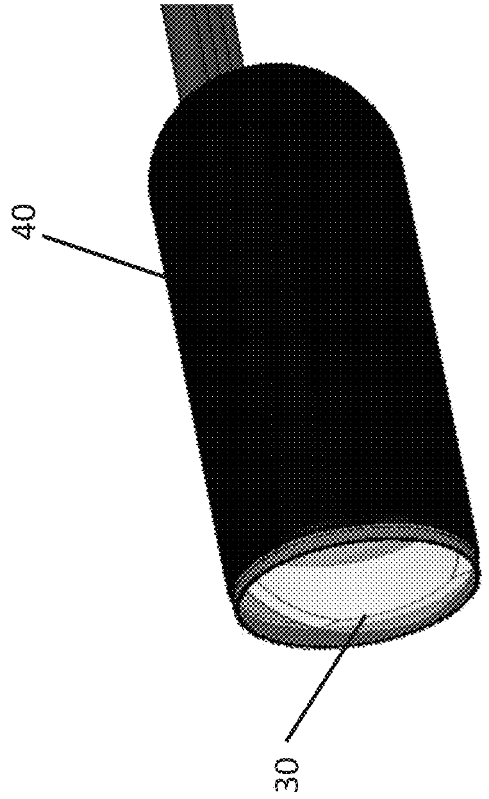
FIG. 5 illustrates the camera and sled as illustrated in FIGS. 4A-4B with potting compound and/or covering.

FIG. 5 illustrates the covering 40 over the cylindrical assembly formed by the sled 20, camera 22, potted housing 24 and prism 30. The covering 40 may be a heat shrink to surround the cylindrical assembly and/or potting compound. The system provides off-axis viewing at the distal end by utilizing a refractive prism 30. For example, the off-axis viewing can provide an angled view by at least 25 degrees. The prism 30 is coupled to the camera 22 through a sled 20. The sled 20 is configured to receive both the prism 30 and the camera 22. The prism 30 can be flat at the end of the sled 20. The cyllindrical assembly can be positioned at the distal end of the elongated body of the tissue visualization device 4.

In some examples, the tissue visualization device 4 can include one or more illumination elements configured to illuminate a target tissue location so that the location can be visualized. A variety of different types of light sources may be employed as illumination elements, so long as their dimensions are such that they can be positioned at or carry light to the distal end of the elongated body. The light sources may be integrated with a given component (e.g., elongated body) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an inter-related whole. The light sources may be light emitting diodes configured to emit light of the desired wavelength range, or optical conveyance elements, e.g., optical fibers, configured to convey light of the desired wavelength range from a location other than the distal end of the elongated body, e.g., a location at the proximal end of the elongated body within the hand piece, to the distal end of the elongated body.

The illumination fiber (not shown) can be placed circumferentially around the cylindrical assembly. This configuration of the prism 30 allows the image of the desired object to be refracted through the prism 30 to achieve the desired off-axis angled view, without the light from the illumination fibers scattering into the image and reducing the image quality. The prism 30 bends the image of the desired object at an angle to be received by the camera 22, rather than bending the light from the illumination fibers onto the desired object.

Figure 6:
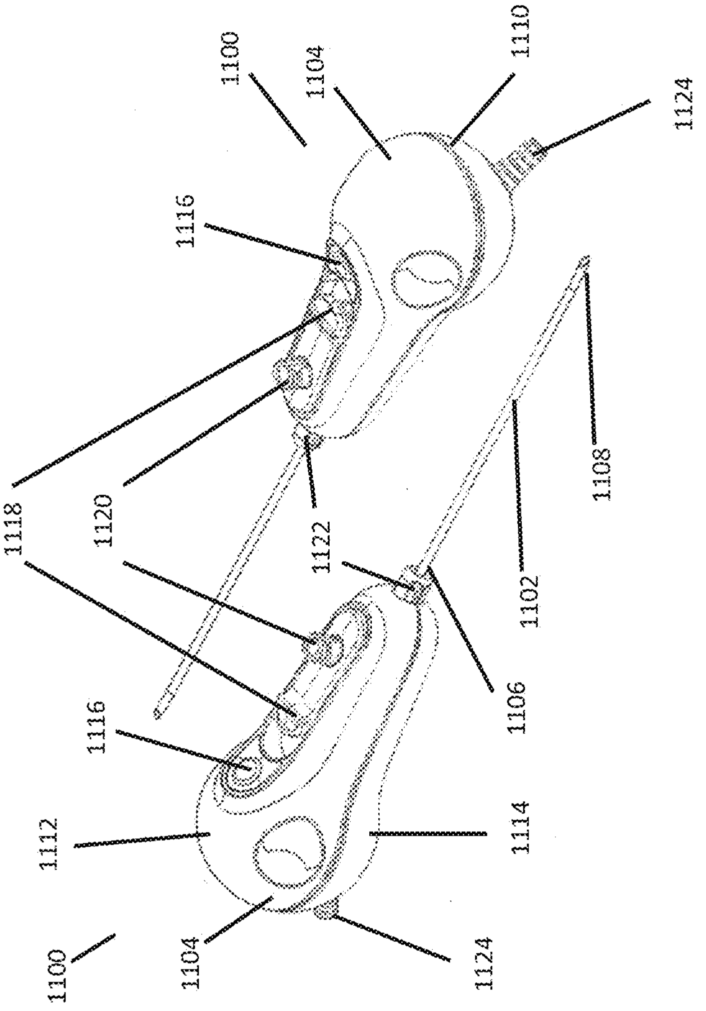
FIG. 6 illustrates an embodiment of a tissue visualization device.

FIG. 6 illustrates an embodiment of a tissue visualization device 1100, comprising an elongated body 1102 and a handpiece 1104. The elongated body may have a length that is at least around 1.5 times longer than its width, at least around 2 times longer than its width, at least around 4 times longer than its width, at least around 10 times or longer than its width, at least around 20 times longer than its width, at least around 30 times longer than its width, at least around 50 times longer than its width, or longer than 50 times the width. The length of the elongated body may vary, and in some instances may be at least around 2 cm long, at least around 4 cm long, at least 6 cm long, at least 8 cm long, at least 10 cm long, at least 15 cm long, at least 20 cm long, at least 25 cm, at least 50 cm, or longer than 50 cm. The elongated body may have the same outer cross-sectional dimensions (e.g., diameter) along the entire length. Alternatively, the cross-sectional diameter may vary along the length of the elongated body. In certain embodiments, the outer diameter of the elongated body is approximately 0.1 to 10 mm, approximately 0.5 mm to 6 mm, approximately 1 mm to 4 mm, approximately 1.5 mm to 3 mm, approximately 2 mm to 2.5 m, or approximately 2.1 mm In certain embodiments, the elongated body is a 13.5 gauge needle, having an OD of about 2.3 mm and a ID of about 1.8 mm In certain embodiments, and as described elsewhere in the specification, the elongated body may have a proximal end 1106 and a distal end 1108. The term "proximal end", as used herein, refers to the end of the elongated body that is nearer the user (such as a physician operating the device in a tissue modification procedure), and the term "distal end", as used herein, refers to the end of the elongated body that is nearer the internal target tissue of the subject during use. The elongated body is, in some instances, a structure of sufficient rigidity to allow the distal end to be pushed through tissue when sufficient force is applied to the proximal end of the elongated body. As such, in these embodiments the elongated body is not pliant or flexible, at least not to any significant extent. In certain embodiments, the distal end 1108 can further comprise a sharpened tip as depicted in FIG. 6, allowing the distal end to pierce through tissue such as a joint capsule. In certain embodiments, the distal end may be pushed from the exterior of the body into the joint capsule, by piercing through the skin and underlying tissues.

Similar to the elongated body of the tissue visualization device 4 of FIG. 1, the elongated body 1102 of the handpiece 1104 of FIG. 6 may include a refractive prism to achieve increased off-axis viewing. The refractive prism may be mounted in a cylindrical assembly, as described and shown in FIGS. 2-5, to provide off-axis viewing at the distal end 1108 of the elongated body 1102.

As depicted in FIG. 6, in embodiments, the handpiece may have a rounded "clamshell" shape comprising a seam 1110 connecting a clamshell top 1112 and a clamshell bottom 1114. In some embodiments, the clamshell top 1112 and bottom 1114 and can be manufactured in two pieces and then attached together at the seam 1110. The rounded clamshell shape provides a comfortable and ergonomic handle for a user to hold while using the device. In certain embodiments and as will be described in greater detail later, the handpiece may comprise an image capture control such as a button 1116 configured to capture a desired image. In further embodiments, the image capture control may comprise a switch, dial, or other suitable mechanism.

The handpiece 1104 may further comprise a retraction control 1118 that retracts or extends a portion of the elongated body 1102 such as a sharpened needle. In certain embodiments, the control 1116 may selectively activate the acquisition of an image and/or video. The control 1116 may thus be configured to selectively start video recording, stop video recording, and/or capture a still image either during video recording or while video recording is off. In some embodiments, the control or another control may turn on/off an ultraviolet light (UV) source that would be used with UV sensitive material such as a gel. For example, a UV-sensitive liquid could be delivered to a target tissue, such as the knee, followed by application of UV liquid to solidify the liquid into a solid or semi-solid material. UV light may be generated via a standard LED, such as those described elsewhere in the specification. The UV light could be directed towards the target tissue via illumination fibers such as those described elsewhere in the specification, while still retaining some illumination fibers to illuminate the target tissue for the purposes of imaging.

In embodiments, the handpiece may comprise a luer connection 1120, configured to connect to any fluid source as described herein this section or elsewhere in this specification, such as sterile saline. The luer connection 1120 may be in fluid communication with a lumen extending throughout the length of the elongated body, allowing for the delivery of fluid or agents to the tissue site.

The junction between the handpiece 1104 and the elongated body 1102 may include a hub 1122 that connects the handpiece 1104 to the elongated body 1102. In some embodiments, the hub may be detachable, allowing the elongated body to be detached from the handpiece. In other embodiments, the elongated body is permanently attached to the handpiece via the hub to provide an integrated assembly.

The handpiece may further comprise a strain relief node 1124, configured to attach to an electrical cable (not shown in FIG. 6). The strain relief node 1124 can serve to reduce strain on electrical wiring that may be in electrical communication with the handpiece.

In some embodiments, the tissue visualization device 1100 is configured as an integrated assembly for one time use. In certain embodiments, the tissue visualization device 1100 is pre-sterilized, thus the combination of integration and pre-sterilization allows the tissue visualization device to be ready for use upon removal from the packaging. Following use, it may be disposed. Thus the handpiece 1104, elongated body 1102, and other components, such as the cable, may be all one integrated unit. By one integrated unit, it is meant that the various portions described above may be attached together as one single piece not intended for disassembly by the user. In some embodiments, the various portions of the integrated unit are inseparable without destruction of one or more components. In some embodiments, the display, as described herein this section or elsewhere in the specification, may also be incorporated and sterilized as part of a single integrated tissue visualization device.

Figure 7:
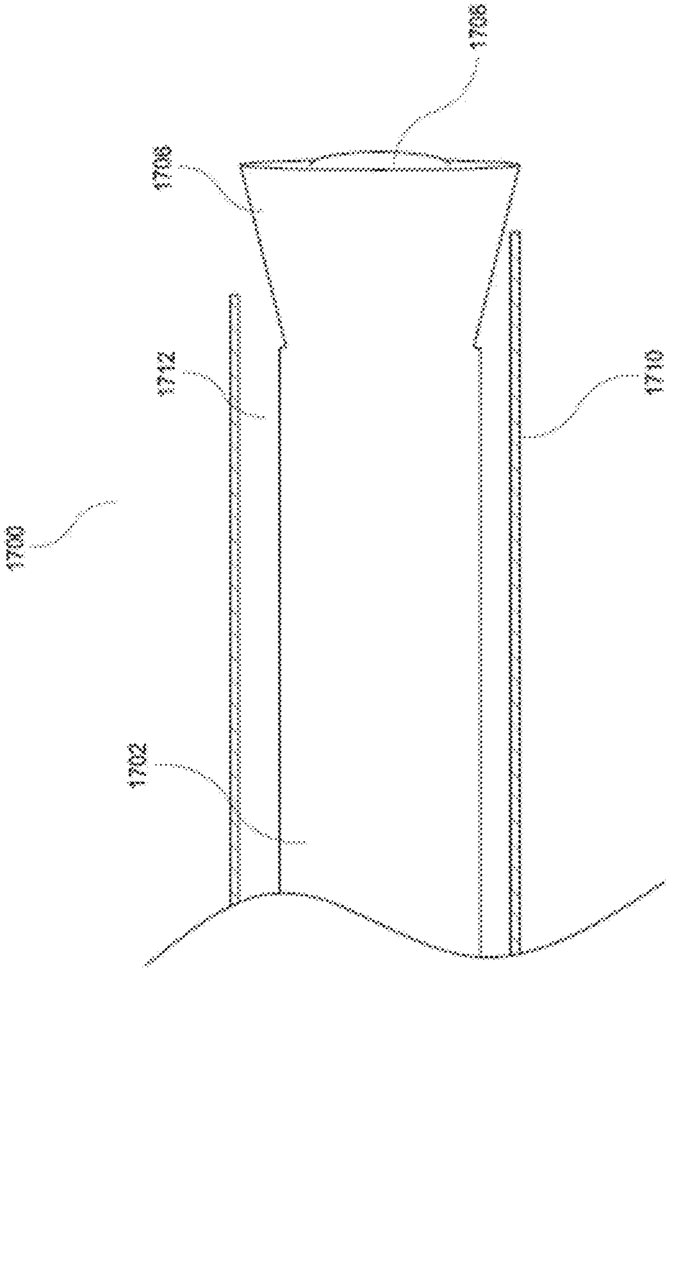
FIG. 7 illustrates a close-up cross-sectional side views of embodiments of the distal end of the tissue visualization device illustrated in FIG. 6.

As shown in FIG. 7, in certain embodiments of the distal end of the elongated body 1700, the distal end of the optical hypotube 1702 may be flared 1706 to accommodate a larger component 1708 positioned at the distal end of the optical hypotube 1702 than would ideally fit into the diameter of a standard hypotube 1704. The larger component 1708 may be a sensor. The larger component 1708 may include a refractive prism for off-axis viewing, as described herein. The larger component 1708 may also be a cylindrical assembly including the sled 20, camera 22, potted housing 24, and prism 30 as described in FIGS. 2-5.

This flare 1706 could simply be a larger diameter cross-section, a square cross section or something to match what is within. The axial length of this flare would be to accommodate the length of the sensor or cylindrical assembly plus routing of illumination fiber around the sensor or cylindrical assembly and would have a transition zone back to the circular cross section of the normal hypotube. In certain embodiments, this may be accomplished with a non-circular cross-section. The sharpened tip may be flared with or without a gap to provide a lumen between the optical hypotube's "OD" and the elongate member's "ID". In some examples, the sharpened tip may be not flared. In certain embodiments, the outer tubular body may be curved such as disclosed herein this section or elsewhere in the specification or the outer tubular body may be straight to accommodate the flared tip.

As described above in relation to the "flared" embodiment, in order to minimize the overall size of the product/needle, the inner diameter (ID) of the outer tubular body may be sized so that it is completely "filled" by the outer diameter(OD) of the flared distal end of the optical hypotube. In embodiments, the flared geometry restricts the inner lumen and prevents the passage of fluid from the end of the outer tubular body.

In embodiments, to allow for fluid flow, the axial length of the flare geometry may be designed to be shorter than the translation distance of the outer tubular body 1710. When the outer tubular body is in the forward or sharp position, the flare is contained within the inner diameter of the tubular body and flow is restricted through the lumen 1712. However, when the tubular body is the retracted position (and blunted), the flared portion of the hypotube completely protrudes out of the open bevel of the tubular body, thereby allowing the effective lumen of the device to be between the normal cross-section of the hypotube and the ID of the needle. In some embodiments, the outer tubular body may contain axial holes to allow for fluid flow from the lumen in a different direction and location from the open end of the elongate body.

Figure 8A:
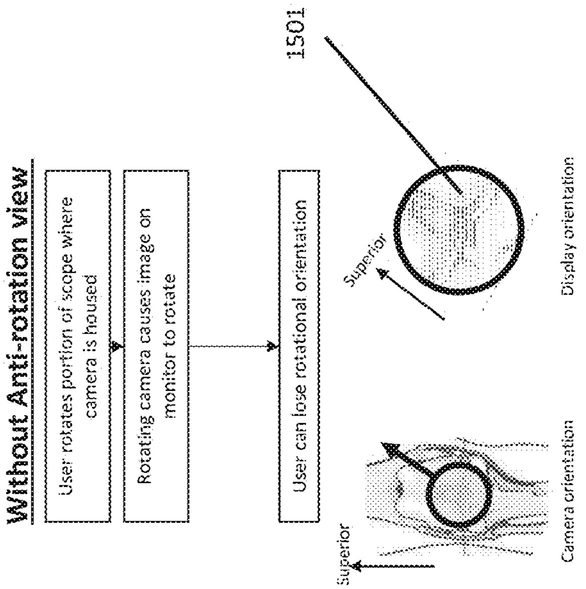
FIGS. 8A-B illustrates embodiments of images with or without rotational image stabilization.
Figure 8B:
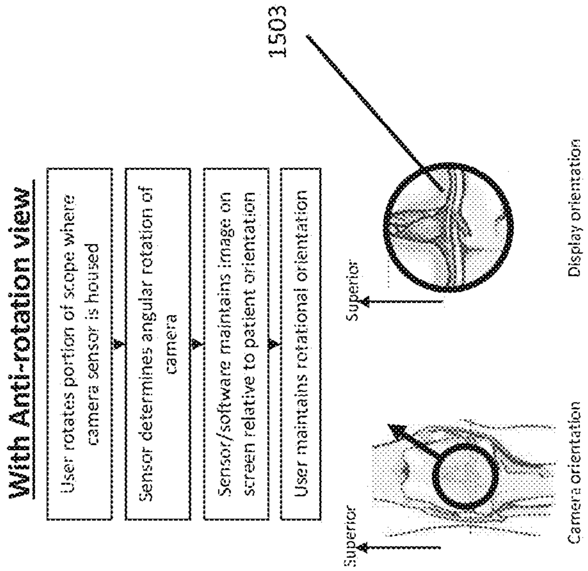

As illustrated in FIG. 1 and FIG. 8A, one consequence of the integrated visualization device is that rotation of the visualization device 4 about the central longitudinal axis to achieve the enlarged field of view will simultaneously cause a rotation of the apparent inferior superior orientation as seen by the clinician on the display such as video screen 19 of FIG. 1 or image 1501 of FIG. 8A. It may therefore be desirable to compensate such that a patient reference direction such as superior will always appear on the top of the screen 19, regardless of the rotational orientation of the visualization device 4, such as depicted in image 1503 of FIG. 8B.

This may be accomplished by including one or more sensors or switches carried by the visualization device 4, which is capable of generating a signal indicative of the rotational orientation of the visualization sensor or camera 22. The visualization device 4 may include a refractive prism for off-axis viewing. The visualization system 4 may include the cylindrical assembly including the refractive prism 30, camera 22, potted housing 24, and sled 20 as described in FIGS. 2-5. The visualization device 4 can also include further sensors, such as simple tilt or orientation sensors such as mercury switches, or other systems capable of determining rotational orientation relative to an absolute reference direction such as up and down. Alternatively, the rotational orientation image correction system may comprise a 3-axis accelerometer with associated circuitry such as a small accelerometer constructed with MEMS (micro-electro mechanical systems) technology using capacitance measurement to determine the amount of acceleration, available from Freescale Semiconductor, Inc., of Austin, Tx and other companies.

As an alternative or in addition to the accelerometer, the visualization device 4 may carry a gyroscope such as a three-axis gyroscope. The output of the gyroscope may be the rate of change of roll angle, pitch angle and yaw angle and rotational rate measurements provided by the gyroscope can be combined with measurements made by the accelerometer to provide a full six degree-of-freedom description of the sensor's motion and position, although that may not be necessary to simply correct for rotational orientation.

The signal from the one or more sensors can be transmitted via wire or wireless protocol to the controller 6 for processing and correction of the rotational orientation of the image on screen 19 or other display, to stabilize the image.

A control may be provided on the hand piece or controller 6, allowing the clinician to select what reference orientation (e.g., patient superior, inferior, true up or down, etc. or true sensor view such that the image on the screen rotates with the sensor) they would like to have appearing at the top of the screen regardless of sensor orientation. In certain embodiments, markers such as an arrow or line may be projected onto the image to further identify different orientations and/or directions.

In some embodiments, the optical hypotube may be sheathed in heat shrink tubing. For example, the outer tubular body as described elsewhere in the specification, may be constructed from a heat-sensitive material. Thus, to construct the elongated body as described elsewhere in the specification, the optical hypotube and other components may be extended down an over-sized outer tubular body which is then shrunk down to the diameter of the optical hypotube via means such as heat, UV, chemical, or other means. In contrast, traditional endoscopes and some endoscopes described elsewhere in the specification house the optics in a rigid stainless steel tube. However, housing the optics within a stainless steel tube may require forcing many optical and illumination fibers down a very tight ID and then applying an adhesive such as epoxy. Such a process is difficult and costly.

Figure 9A:
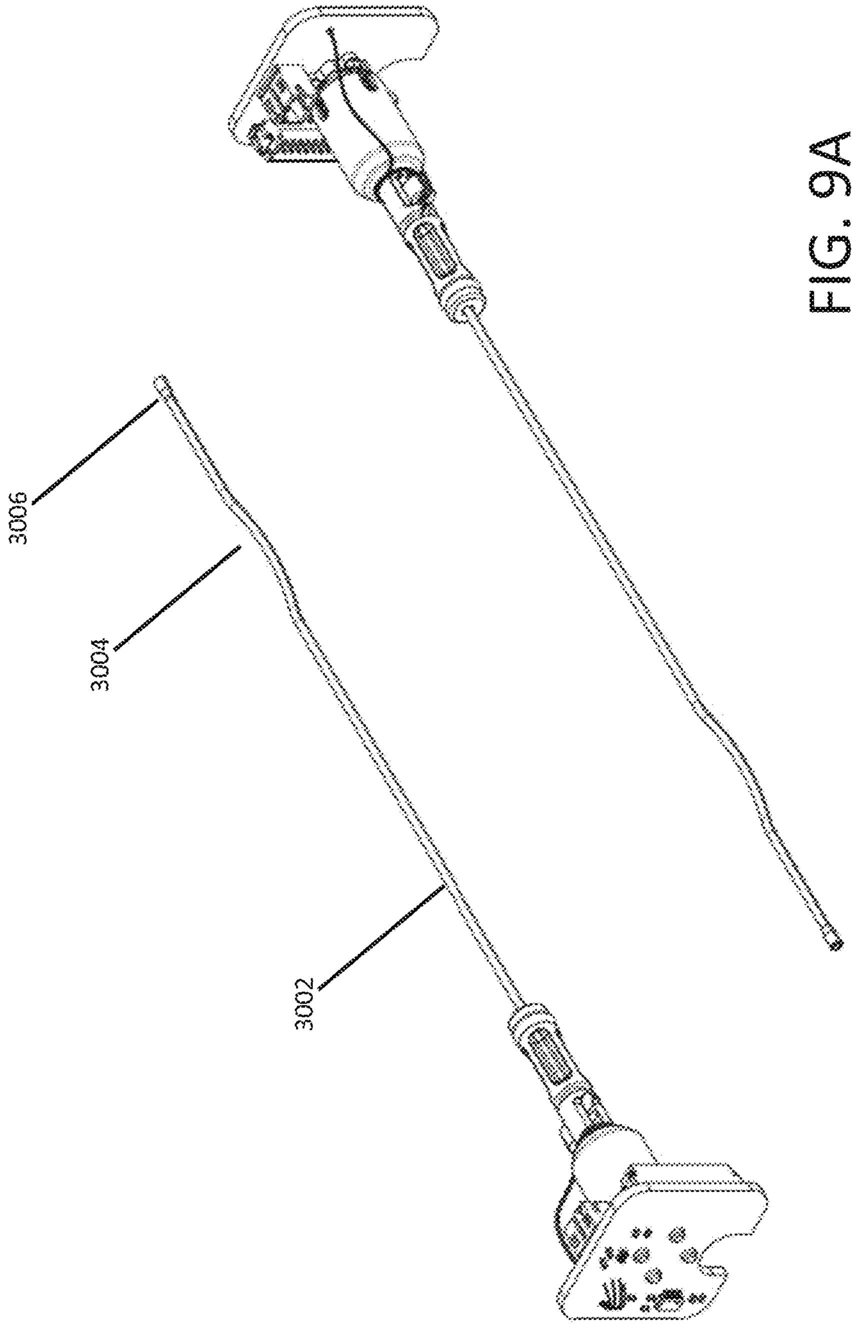
FIGS. 9A-C depict embodiments of a tissue visualization device comprising bent optical hypotubes.

FIG. 9A depicts an embodiment of an inner optical hypotube 3002, similar to the optical hypotubes depicted previously in FIG. 7. Here, the optical hypotube is shown without the outer tubular body; however, in use the optical hypotube would be contained within an outer tubular body as shown in FIG. 7. In embodiments, the optical hypotube may have a bend 3004, the bend biasing the distal end 3006 of the optical hypotube against the outer tubular body, when the optical hypotube is contained within an outer tubular body. In certain embodiments, the bend may be positioned about 50% down the length of the optical hypotube from the handpiece, about 60%, about 70%, about 80%, or about 90%. In certain embodiments the bend may be a gradual bend, wherein other embodiments the bend may be a sharp bend. In embodiments, there may be a single bend, two bends, three bends, four bends, five bends, or more than five bends. In certain embodiments, a bend may have a degree of bending of at least about: 1 degree, 5 degrees, 10 degrees, 15 degrees, 25 degrees, 35 degrees, 45 degrees, 50 degrees, 60 degrees, 75 degrees, or 90 degrees.

The distal end 3006 of the inner optical hypotube 3002 may include a refractive prism for off-axis viewing, as described herein. The distal end 3006 may include a cylindrical assembly including the refractive prism 30, camera 22, potted housing 24, and sled 20 as described in FIGS. 2-5.

Figure 9B:
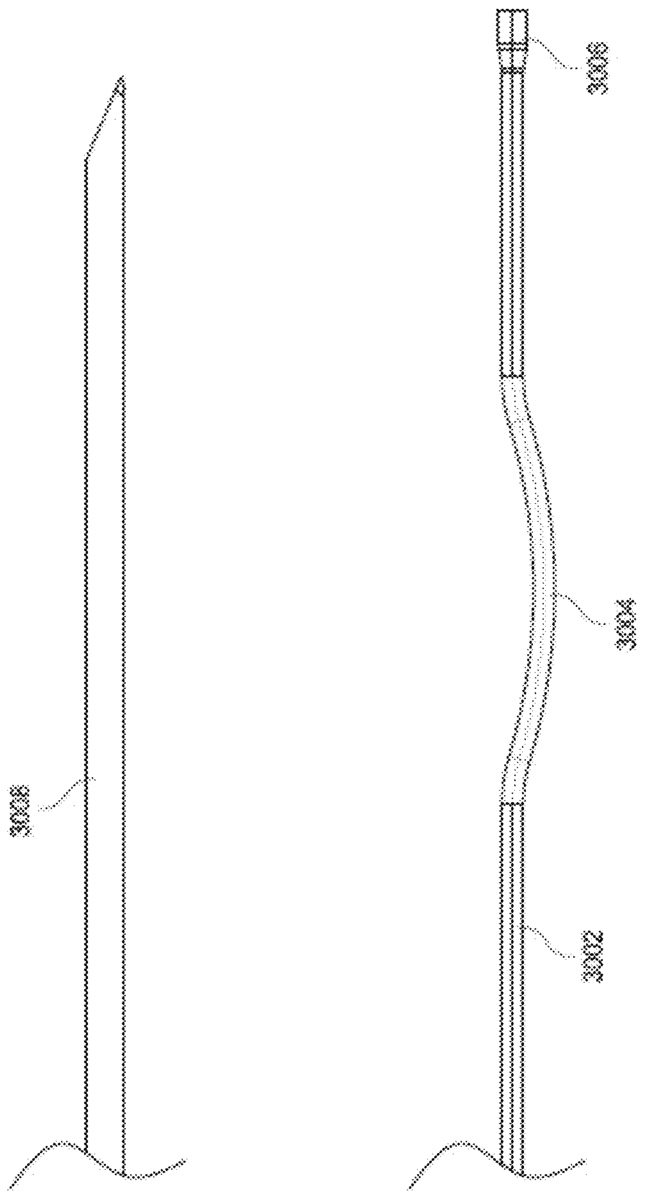
Figure 9C:
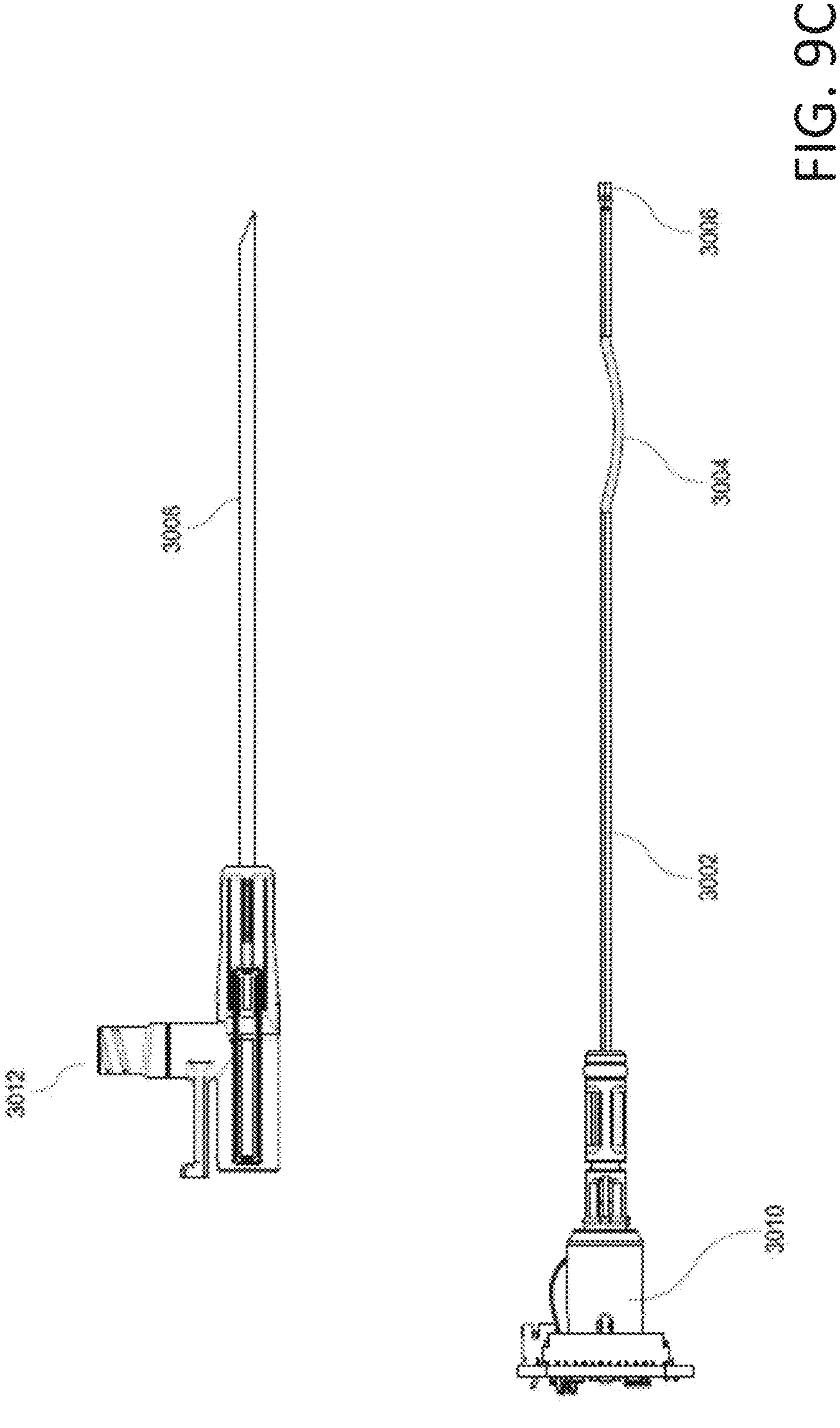

FIG. 9B is a photograph of embodiments of the optical hypotube 3002 side by side with an embodiment of an outer tubular body 3008, similar to the outer tubular bodies depicted previously in FIG. 7. Here, the bend 3004 may be fairly gradual, biasing the tip 3006 against the sharpened distal end of the outer tubular body 3008. FIG. 9C further depicts embodiments of the optical hypotube 3002 and the outer tubular body 3008, however, here the needle hub assembly 3012 and the electro-optical assembly 3010 are shown, similar to the embodiments described above in relation to FIG. 7.

Figure 10A:
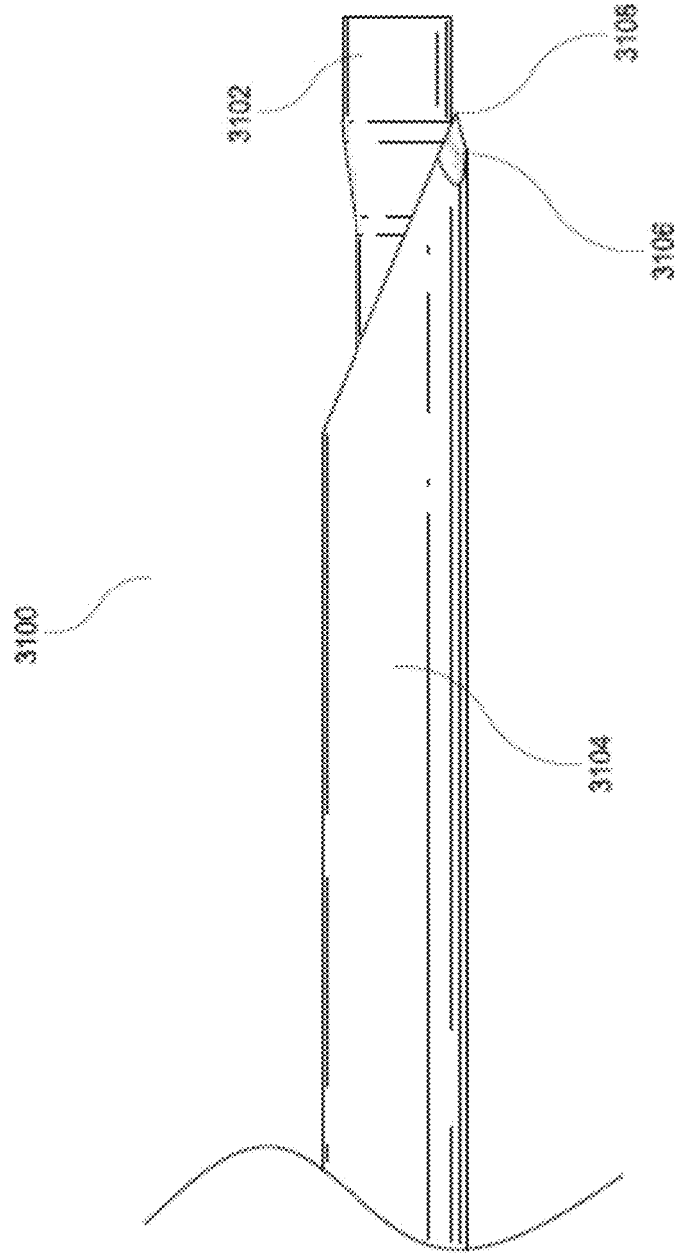
FIGS. 10A-B are a photograph and illustration of embodiments of the distal tip of a tissue visualization device.
Figure 10B:
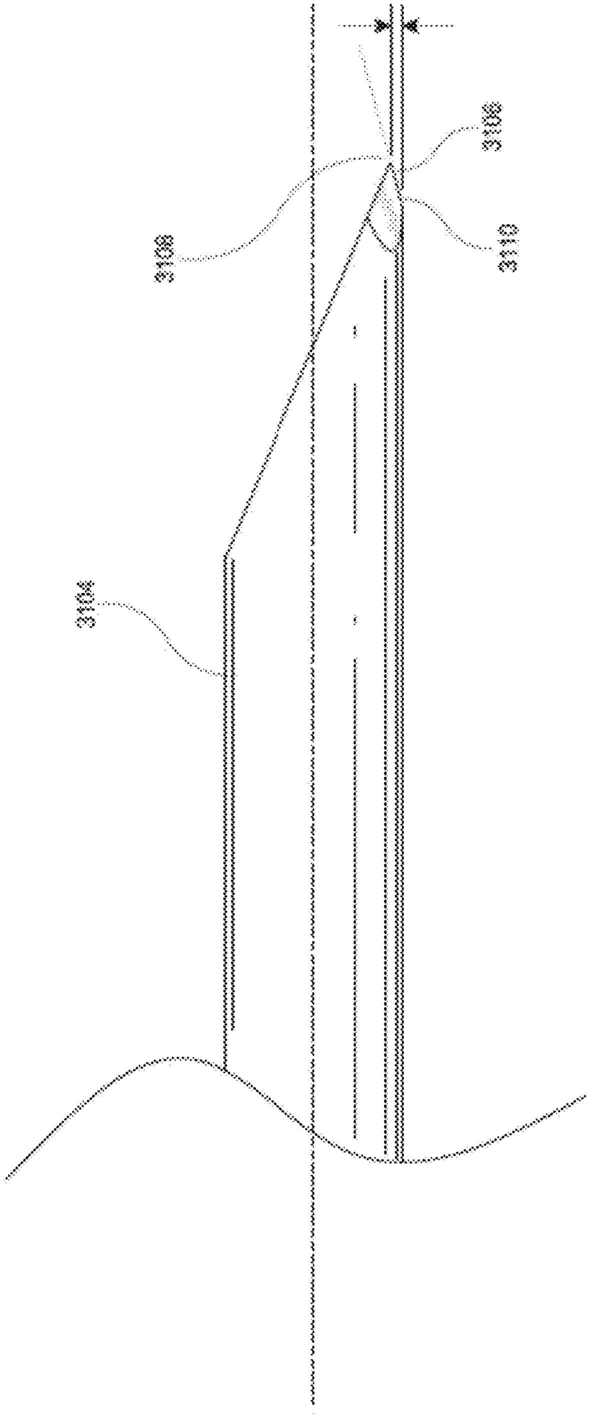

FIG. 10A is a close-up photograph of an embodiment of the distal end of the elongate body 3100, similar to those described previously, comprising outer tubular body 3104 and optical hypotube 3102. Here, the outer tubular body 3104 is retracted and blunted as will be described further below. As described previously, the elongate body has a reverse grind 3106 bringing the needle point 3108 closer to the optical hypotube. As shown in FIGS. 9A-B, the Optical Hypotube bending biases it against the inner diameter of the outer tubular body 3104, closest to the point of the sharpened tip 3108. As shown in previous embodiments, when the outer tubular body is retracted, it may be blunted against the optical hypotube 3102. FIG. 10B depicts a close-up view of an embodiment of the distal end of the outer tubular body 3104, similar to the embodiments described previously. Here, the reverse grind on the outer tubular body, raises the sharpened tip upward, allowing the sharpened tip to be better blunted by the optical hypotube. In certain embodiments, the reverse grind may raise the sharpened tip upward by angle 3110. In certain embodiments, the angle may be about: 5 degrees, 10 degrees, 15 degrees, 25 degrees, 30 degrees, 45 degrees, 60 degrees, 75 degrees, 90 degrees, or more than 90 degrees.

The distal end of the optical hypotube 3102 may include a refractive prism for off-axis viewing, as described herein. The distal end may include a cylindrical assembly including the refractive prism 30, camera 22, potted housing 24, and sled 20 as described in FIGS. 2-5.

In certain embodiments, the blunting contact between the optical hypotube 3102 and the outer tubular body 3104 may generate a tangential contact force. In some embodiments, a Huber type bend in the outer tubular body may result in tangential contact with the optical hypotube and deflect the hypotube to provide a contact force that provides blunting as the resistance to this force may need to be overcome before the optical hypotube no longer blunts the sharpened tip. In certain embodiments, the outer tubular body may comprise a long bend in needle to bias the optical hypotube towards the direction of bend of the outer tubular body for example, in certain embodiments, a bend may have a degree of bending of at least about: 1 degree, 5 degrees, 10 degrees, 15 degrees, 25 degrees, 35 degrees, 45 degrees, 50 degrees, 60 degrees, 75 degrees, or 90 degrees.

In certain embodiments, a thin-wall component may be attached to the optical hypotube to bias the optical hypotube in a certain direction and/or orientation. This component may have a larger diameter than the distal portion of the optical hypotube and could optionally be attached to the outer surface of the optical hypotube, for example at a point/line on the lower most portion of the outer diameter. This component may be in the form of a tube along the outside of the optical hypotube but in certain embodiments may have portions removed to minimize the impact to the lumen or fluid path. In certain embodiments, the thin wall component could be located at position proximal to the flare in the optical hypotube. Low profile “fingers” may be used to center the hypotube within the needle.

Figure 11:
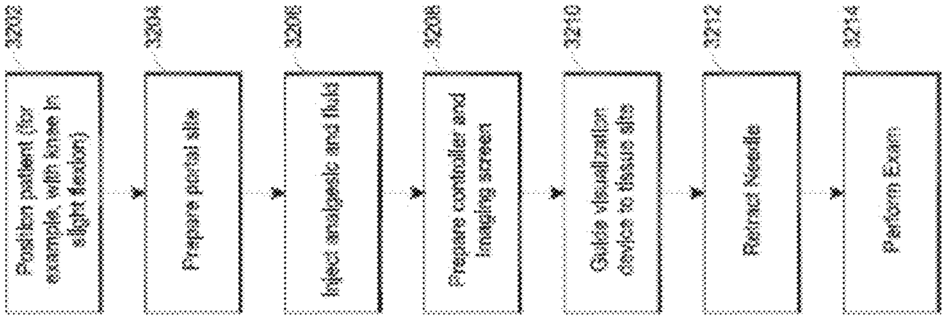
FIG. 11 depicts embodiments of a method for visualization an internal tissue site.

FIG. 11 is a flowchart showing an embodiment of a method for treating a tissue site in the knee using the apparatuses disclosed herein this section and throughout the specification. However, as will be understood by one of skill in the art, the method may be suitable for any type of joint and other tissue types. For example, the method may rely upon tissue visualization devices and systems such as shown in the previous figures, such as FIG. 1. In the first step, 3202, the patient may be positioned either supine or seated, with a joint in slight flexion. In the second step 3204, the portal site is prepared with a local aseptic solution. Next analgesic is delivered to the joint 3206 and the joint is filled with a minimum of 30 cc of sterile fluid. In the fourth step 3208, the controller and viewing screen are turned on and the visualization device is connected to the controller and screen. Additionally, a stopcock and syringe may be attached to the visualization device. Next, the visualization device is inserted into the inferolateral or inferomedial portal, based on suspected pathology and guided to the tissue site 3210. The visualization device may be inserted directly into the lateral or medial compartment, avoiding the “notch” and fat pad. Once inside the joint capsule, the sharpened tip of the outer tubular body or “needle” is retracted via the retraction button 3212. Lastly, a medical practitioner may perform an exam 3214 using the visualization device by applying varus and valgus tension on the tibia to allow for medial and lateral distention. Further, extending the knee allows for the posterior compartment to be more easily visualized. Additional sterile saline may be injected at any time as needed throughout the exam to clear the field of view.

The distal end of the visualization device may include a refractive prism for off-axis viewing, as described herein. The distal end may include a cylindrical assembly including the refractive prism 30, camera 22, potted housing 24, and sled 20 as described in FIGS. 2-5. Once in position, when the distal end is positioned within a desired area of treatment, the user can see the desired area of treatment at a wider angle.

In certain embodiments, while the visualization device is navigating toward the tissue site, the optical hypotube may remain retracted within the outer tubular body, allowing for a "tunnel" view of the tissue outside the outer tubular body. This approach advantageously reduces soft tissue interaction with the optical hypotube and provides an offset from the distal end, allowing for improved visualization in some cases. In certain embodiments, additional fluid may be added to the joint (such as a knee) to improve visualization by clearing debris and creating space for the optical components. Fluid may be added to the knee via a secondary needle to pre-condition the knee for visualization, prior to insertion of the visualization device. In some embodiments, fluid may be added to the knee through the visualization device while the outer tubular body is still in the forward position. Constant fluid may also be added via a syringe, such as by the physician or via an extension tube plus syringe depressed by an assistant. In some embodiments, short bursts of fluid (1-2m1) may be applied to clear the area immediately in front of the visualization device.

With respect to imaging the interior of a joint capsule, methods include positioning a distal end of the visualization element of the invention in viewing relationship to the target tissue. By viewing relationship is meant that the distal end is positioned within 40 mm, such as within 10 mm, including within 5 mm of the target tissue site of interest. Positioning the distal end of the viewing device in relation to the desired target tissue may be accomplished using any convenient approach, including direct linear advance from a percutaneous access point to the target tissue. Following positioning of the distal end of the imaging device in viewing relationship to the target tissue, the target tissue is imaged through use of the illumination elements and visualization sensors (e.g. the camera) to obtain image data. Image data obtained according to the methods of the invention is output to a user in the form of an image, e.g., using a monitor or other convenient medium as a display means. In certain embodiments, the image is a still image, while in other examples the image may be a video.

In embodiments, the internal target tissue site may vary widely. Internal target tissue sites of interest include, but are not limited to, orthopedic joints, cardiac locations, vascular locations, central nervous system locations, etc. In certain cases, the internal target tissue site comprises spinal tissue. Orthopedic joints may comprise any type of joint of interest within the human body, such as the knee or the shoulder. In some embodiments, the internal tissue site may comprise sites of interest during general surgery, such as abdominal organs and/or surrounding tissues.

Further applications of the tissue visualization devices described herein this section or elsewhere in the specification include use in general surgery (laparoscopic or other minimally invasive surgery) as a secondary visualization device. In some instances, the laparoscopic camera may need to be removed and the procedure is blind. However, the outer diameters of the devices described herein this application are small enough that they can be used to eliminate blackout once a laparoscopic camera is removed. In such embodiments, the elongated body is no longer rigid, instead the body is flexible and can be mounted in an elongated flexible tubular body with any of a variety of steering mechanisms such as one or two or three or more pull wires to deflect the distal end. In some embodiments, the device may comprise a biased curved distal end (e.g., Nitinol) that can be selectively curved or straightened by retracting an outer straight sleeve or internal straightening wire, etc.

Beyond general surgery and the other applications described herein this section and elsewhere in the specification, embodiments of the visualization devices described herein can be utilized in ear, nose, and throat applications. For example, the devices described herein may be used in any diagnostic evaluation where visualization may be valuable. As another example, the devices described herein may also be used to guide or evaluate the treatment of chronic sinusitis, for instance, the dilatation of a sinus such as the maxillary sinus.

In some embodiments, the subject devices and methods find use in a variety of different applications where it is desirable to image and/or modify an internal target tissue of a subject while minimizing damage to the surrounding tissue. The subject devices and methods find use in many applications, such as but not limited to surgical procedures, where a variety of different types of tissues may be visualized and potentially treated, including but not limited to; soft tissue, cartilage, bone, ligament, etc.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. An integrated disposable tissue visualization device with off axis viewing, comprising:
- an elongate rigid tubular probe, extending along a longitudinal axis between a proximal end and a distal end;
- a camera;
- an illumination element;
- a prism; and
- a sled configured to receive the camera and the prism,
- wherein the sled comprises a distal angled surface at distalmost face, the angled surface configured to receive the prism,
- wherein the prism provides off-axis viewing of a target tissue at an angle range of about 25 degrees to about 30 degrees, and
- wherein the prism comprises high index of refraction material of at least 2.0.

2. The device of claim 1, wherein the camera is positioned within an enclosed area of the sled.

3. The device of claim 1, wherein the prism comprises an angled surface configured to be positioned on the angled surface of the sled.

4. The device of claim 3, wherein a slope of the angled surface of the prism is substantially similar to a slope of the angled surface of the sled.

5. The device of claim 1, wherein the sled, the camera, and a potted housing form a cylindrical assembly.

6. The device of claim 5, wherein the cylindrical assembly further comprises the prism.

7. The device of claim 1, wherein the sled and a potted housing form a cylindrical assembly with the camera positioned therein.

8. The device of claim 7, wherein the distal angled surface of the sled comprises an angled distal surface of the cylindrical assembly.

9. The device of claim 8, wherein the cylindrical assembly further comprises the prism, wherein the prism is positioned on the angled distal surface of the cylindrical assembly.

10. The device of claim 9, wherein the prism comprises a flat surface configured to form a flat distal end of the cylindrical assembly.

11. The device of claim 7, wherein the cylindrical assembly is positioned at the distal end of the elongate rigid tubular probe.

12. The device of claim 7, wherein the illumination element is positioned circumferentially around the cylindrical assembly.

13. The device of claim 7, further comprising a covering that surrounds the cylindrical assembly.

14. The device of claim 1, wherein the illumination element comprises an illumination fiber or light emitting diodes.

15. The device of claim 1, wherein the prism is configured to refract an image of the target tissue to be received by the camera.

16. The device of claim 1, wherein the target tissue comprises an orthopedic joint.

17. The device of claim 1, wherein at least a portion of the prism is distal to the entire sled.

18. The device of claim 1, wherein the distal angled surface comprises an angle of less than 90 degrees.

* * * * *